(12) United States Patent
Liu

(10) Patent No.: US 10,192,423 B2
(45) Date of Patent: Jan. 29, 2019

(54) FAULT DETECTION DEVICES AND FAULT DETECTION METHODS

(71) Applicant: Quanta Computer Inc., Taoyuan (TW)

(72) Inventor: Tai-Jung Liu, Taoyuan (TW)

(73) Assignee: QUANTA COMPUTER INC., Guishan Dist., Taoyuan (TW)

(*) Notice: Subject to any disclaimer, the term of this patent is extended or adjusted under 35 U.S.C. 154(b) by 0 days.

(21) Appl. No.: 15/703,376

(22) Filed: Sep. 13, 2017

(65) Prior Publication Data
US 2018/0336776 A1    Nov. 22, 2018

(30) Foreign Application Priority Data
May 16, 2017    (TW) .............................. 106116066 A

(51) Int. Cl.
| G08B 21/18 | (2006.01) |
| G01J 1/44 | (2006.01) |
| G01N 21/95 | (2006.01) |
| G01J 1/42 | (2006.01) |

(52) U.S. Cl.
CPC .............. *G08B 21/185* (2013.01); *G01J 1/44* (2013.01); *G01N 21/95* (2013.01); *G08B 21/182* (2013.01); *G01J 2001/4247* (2013.01)

(58) Field of Classification Search
CPC ....... G08B 21/185; G08B 21/182; G01J 1/44; G01J 2001/4247; G01N 21/95

USPC ......................................................... 340/635
See application file for complete search history.

(56) References Cited

U.S. PATENT DOCUMENTS

| 2007/0146302 A1* | 6/2007 | Liu ...................... G09G 3/3406 345/102 |
| 2015/0116344 A1* | 4/2015 | Won ........................ G09G 3/32 345/589 |
| 2016/0253944 A1* | 9/2016 | Lu .......................... G09G 3/2003 345/589 |
| 2017/0004754 A1* | 1/2017 | Chin ........................ G09G 3/32 |
| 2017/0352310 A1* | 12/2017 | Kim ....................... G06F 3/1446 |

* cited by examiner

*Primary Examiner* — Jack K Wang
(74) *Attorney, Agent, or Firm* — McClure, Qualey & Rodack, LLP

(57) ABSTRACT

A fault detection device, adapted to an electronic device having a display screen, including a first warning unit, a second warning unit, a first sensor and a microprocessor. The first sensor is arranged in front of the display screen, and obtains and outputs a first current brightness value every first predetermined period of time. The microprocessor is coupled to the first warning unit, the second warning unit, and the first sensor, and compares the first current brightness value with a first previous brightness value. When the first current brightness value is equal to the first previous brightness value, the microprocessor enables the first warning unit to generate a first warning signal. When the first current brightness value is equal to the first previous brightness value for more than a second predetermined period of time, the microprocessor enables the second warning unit to generate a second warning signal.

10 Claims, 5 Drawing Sheets

FAULT DETECTION DEVICES AND FAULT DETECTION METHODS

CROSS REFERENCE TO RELATED APPLICATIONS

This Application claims priority of Taiwan Patent Application No. 106116066, filed on May 16, 2017, the entirety of which is incorporated by reference herein.

BACKGROUND OF THE INVENTION

Field of the Invention

The present invention relates to a fault detection device and a fault detection method, and more particularly, to a fault detection device and a fault detection method for determining whether a display screen is malfunctioning according to a change in brightness value.

Description of the Related Art

When an electronic device enters the production stage, there is usually a problem wherein a part of the electronic device is defective. The existing solutions that improve yield are to assign experienced operators on the production line to monitor and pick out the malfunctioning products for maintenance. However, relying on the human eye to pick out malfunctioning products can result in a higher probability of wrong determinations, and it might take more time, which will occupy the space in the production line, and thus reduce productivity. Therefore, how to quickly and accurately find a malfunctioning electronic device is the problem that needs to be solved immediately.

BRIEF SUMMARY OF INVENTION

An embodiment of the present invention provides a fault detection device, adapted to an electronic device having a display screen, including a first warning unit, a second warning unit, a first sensor and a microprocessor. The first warning unit generates a first warning signal. The second warning unit generates a second warning signal. The first sensor is arranged in front of a display screen of the display, and obtains and outputs a first current brightness value every first predetermined period of time. The microprocessor is coupled to the first warning unit, the second warning unit, and the first sensor, and compares the first current brightness value with a first previous brightness value. When the first current brightness value is equal to the first previous brightness value, the microprocessor enables the first warning unit to generate a first warning signal, and when the first current brightness value is equal to the first previous brightness value for more than a second predetermined period of time, the microprocessor enables the second warning unit to generate a second warning signal. The second predetermined period of time is longer than the first predetermined period of time.

Another embodiment of the present invention provides a fault detection method for an electronic device having a display screen, including the steps of: obtaining, using a first sensor, a current brightness value of one of the display screens a first sensor at a first predetermined period of time, wherein the first sensor is arranged in front of the display screen; receiving, using a microprocessor, the first current brightness value from the first sensor; and comparing, using the microprocessor, the first current brightness value with a first previous brightness value; when the first current brightness value is equal to the first previous brightness value, enabling a first warning unit to generate a first warning signal by the microprocessor; and when the first current brightness value is equal to the first previous brightness value for more than a second predetermined period of time, enabling a second warning unit to generate a second warning signal by the microprocessor; wherein the second predetermined period of time is greater than the first predetermined period of time.

BRIEF DESCRIPTION OF DRAWINGS

The invention can be more fully understood by reading the subsequent detailed description and examples with references made to the accompanying drawings, wherein.

3A to 3C are schematic diagrams of the fault detection device in accordance with the second embodiment of the present invention.

Figure 4:
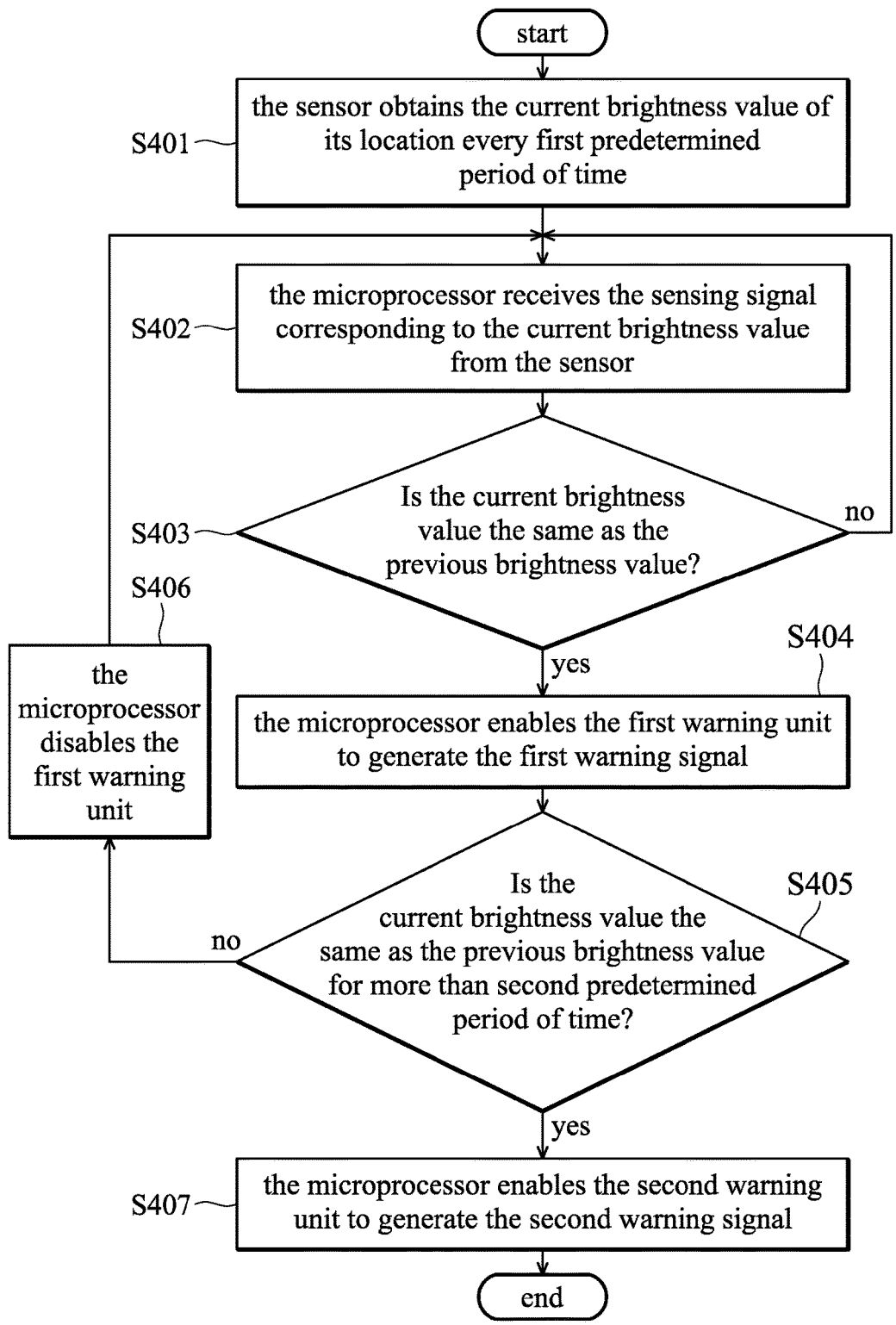

FIG. 4 is a flowchart of a fault detection method in accordance with an embodiment of the present invention.

Figure 5:
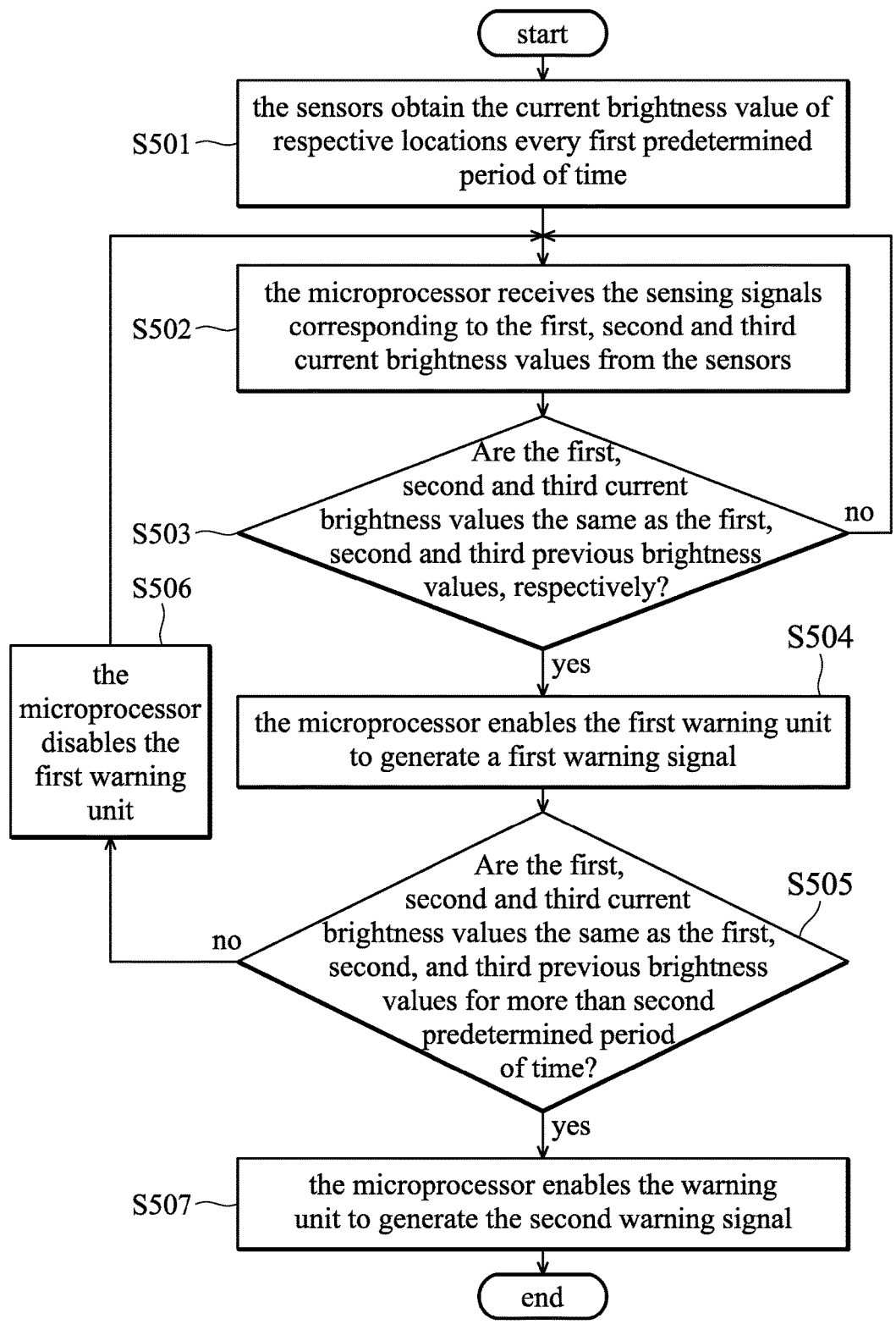

FIG. 5 is a flowchart of the fault detection method in accordance with another embodiment of the present invention.

DETAILED DESCRIPTION OF INVENTION

Further areas to which the present fault detection devices and fault detection methods can be applied will become apparent from the detailed description provided herein. It should be understood that the detailed description and specific examples, while indicating exemplary embodiments of fault detection devices and fault detection methods, are intended for the purposes of illustration only and are not intended to limit the scope of the invention.

Figure 1:
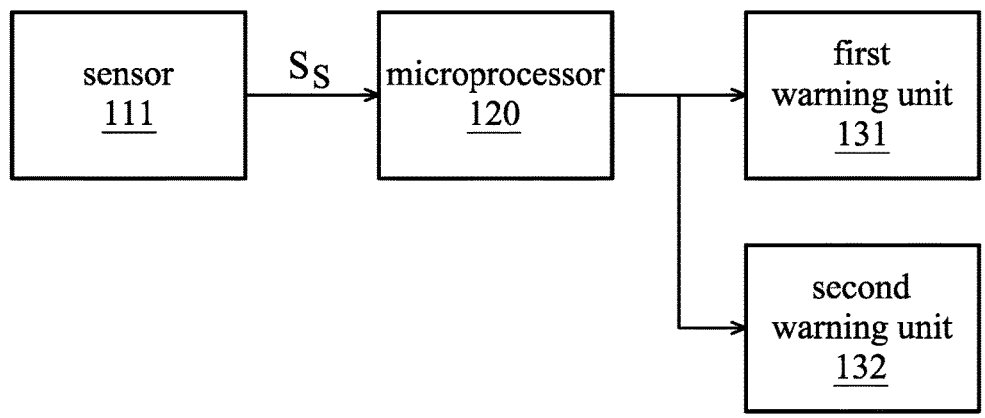
FIG. 1 is a block diagram of a fault detection device in accordance with a first embodiment of the present invention.

FIG. 1 is a block diagram of a fault detection device in accordance with a first embodiment of the present invention. The fault detection device 100 is used to detect whether a display screen is malfunctioning. As shown in FIG. 1, the fault detection device 100 includes a sensor 111, a microprocessor 120, a first warning unit 131 and a second warning unit 132. The sensor 111 obtains and outputs a sensing signal $S_S$ corresponding to a current brightness value of the display screen every first predetermined period of time. The microprocessor 120 is coupled to the sensor 111, and receives the obtained sensing signal $S_S$ from the sensor 111. The microprocessor 120 can be any microprocessors that can convert the sensing signal $S_S$ to a readable brightness value. The first warning unit 131 is coupled to the microprocessor 120. When the microprocessor 120 determines that the brightness value of the display screen is not changed according to the sensing signal $S_S$, the first warning unit 131 is enabled to generate a first warning signal. The first warning unit 131 can be an LED. When the microprocessor 120 enables the first warning unit 131, the first warning unit 131 can blink the LED or keep the LED on as the first warning signal. The second warning unit 132 is also coupled to the microprocessor 120. When the microprocessor 120 determines that the brightness value of the display screen is not changed for more than a second predetermined period of time according to the sensing signal $S_S$, the second warning unit 132 is enabled to generate a second warning signal. The second warning unit 132 can be a buzzer, and when the microprocessor 120 enables the second warning unit 132, the second warning unit can make noise as the second warning signal.

According to a first embodiment of the present invention, the sensor 111 obtains the current brightness value of its location where the sensor is placed on the display screen every predetermined period of time (such as 300 milliseconds) after the fault detection device 100 is enabled, and outputs the corresponding sensing signal $S_S$. After the microprocessor 120 obtains the current brightness value from the sensor 111, the microprocessor 120 reads a previous brightness value from a cache (not shown) and determines whether the current brightness value is the same as the previous brightness value. It should be noted that there is no brightness value stored in the cache of the microprocessor 120, the microprocessor 120 stores the received current brightness value in the cache as the previous brightness value, and makes the determination after receiving the next brightness value. After the microprocessor 120 completes the determination, the previous brightness value is updated according to the current brightness value as the basis for the next determination. When the microprocessor 120 determines that the current brightness value is the same as the previous brightness value, the first warning device 131 enables the first warning signal 131 and outputs the first warning signal (e.g., a flashing the LED). After 300 milliseconds, the microprocessor 120 receives the next brightness value as the current brightness value, and then determines whether the current brightness value is still the same as the previous brightness value. If the current brightness value is different from the previous brightness value, the microprocessor 120 may disable the first warning device 131. On the other hand, if the current brightness value is the same as the previous brightness value, the first warning device 131 is continuously enabled. If the current brightness value is still the same as the previous brightness value (i.e., the brightness value is not changed within 5 minutes) for more than a second predetermined period of time (e.g., 5 minutes), the microprocessor 120 enables the second warning 132 (such as making noise) to indicate the operator that the electronic device is malfunctioning. It should be noted that the length of the first predetermined period of time and the second predetermined period of time can be adjusted according to the types of the display screen or a criteria of the determination, and is not limited to the embodiment of the present invention.

Figure 2:
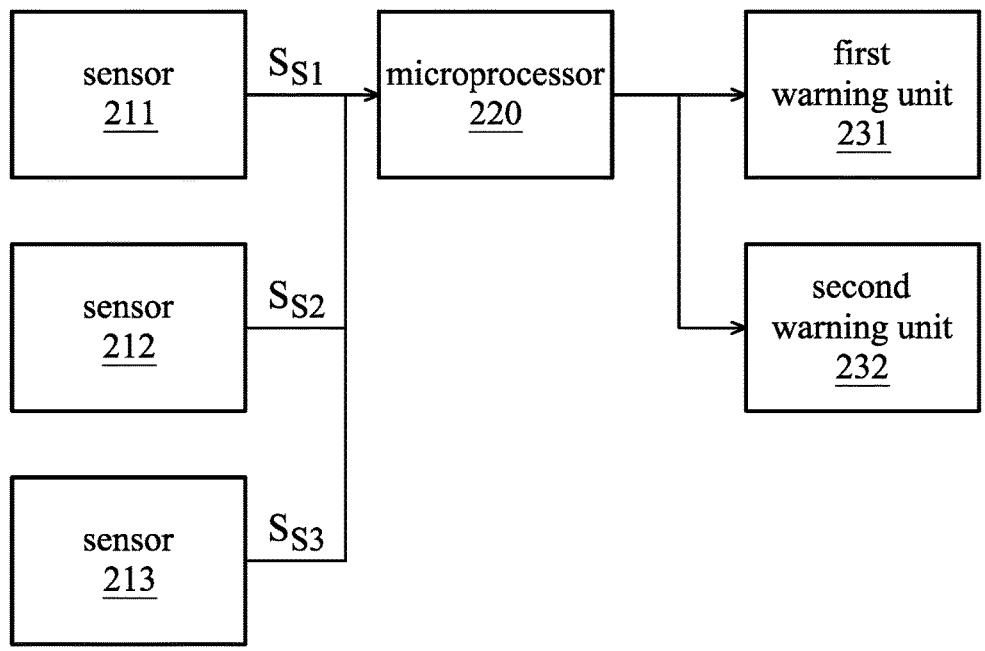
FIG. 2 is a block diagram of a fault detection device in accordance with a second embodiment of the present invention.

FIG. 2 is a block diagram of the fault detection device according to a second embodiment of the present invention. As shown in FIG. 2, the fault detection device 200 has three sensors 211 to 213 for sensing the brightness values of different locations on the display screen, respectively. The functions of the microprocessor 220, the first warning device 231 and the second warning device 232 are the same as the microprocessor 120, the first warning device 131 and the second warning device 132 recited in FIG. 1, thus it is not described here to simplify the description.

In this embodiment, the sensors 211 to 213 sense the current brightness values of respective locations and output the corresponding sensing signals $S_{S1}$ to $S_{S3}$ after the fault detection device 200 is enabled. The microprocessor 220 receives the sensing signals $S_{S1}$ to $S_{S3}$ from the sensors 211 to 213, obtains the first, second and third current brightness values, respectively, and reads the first, second and the third previous brightness value from the cache. Then, the microprocessor 220 determines whether the first, second and third current brightness values are equal to the first, second and third previous brightness values, respectively. Unlike the first embodiment, the microprocessor 220 only enables the first warning unit 231 to output the first warning signal when the first, second, and third current brightness values are equal to the first, second and third previous brightness values at the same time. In other words, when any one of the first, second, and third current brightness values is not equal to the first, second and third previous brightness values, the microprocessor 220 determines that the current operation of the display screen is normal. Likewise, when the first, second and third current brightness values are equal to the first, second and third previous brightness values for more than the second predetermined period of time, the microprocessor 220 enables the second warning unit 232 to output the second warning signal. Compared with the first embodiment, the second embodiment uses three sensors to sense the display screen of different locations, thereby making the determination more accurate.

Figure 3A:
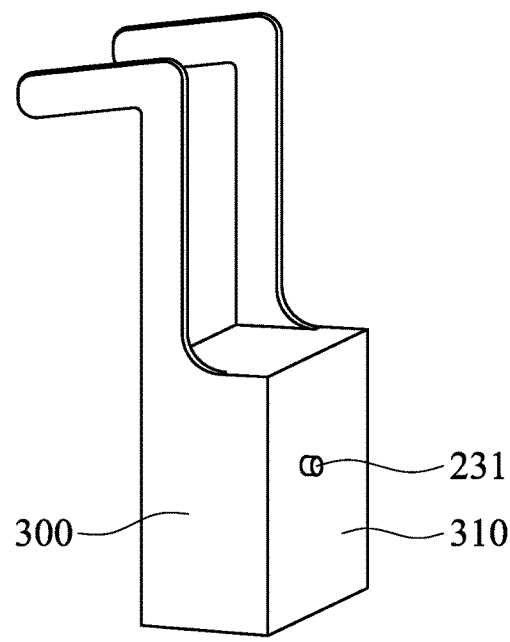
Figure 3B:
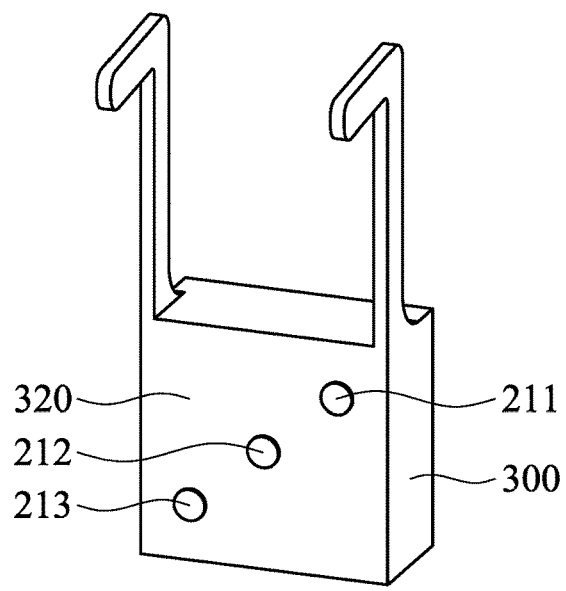
Figure 3C:
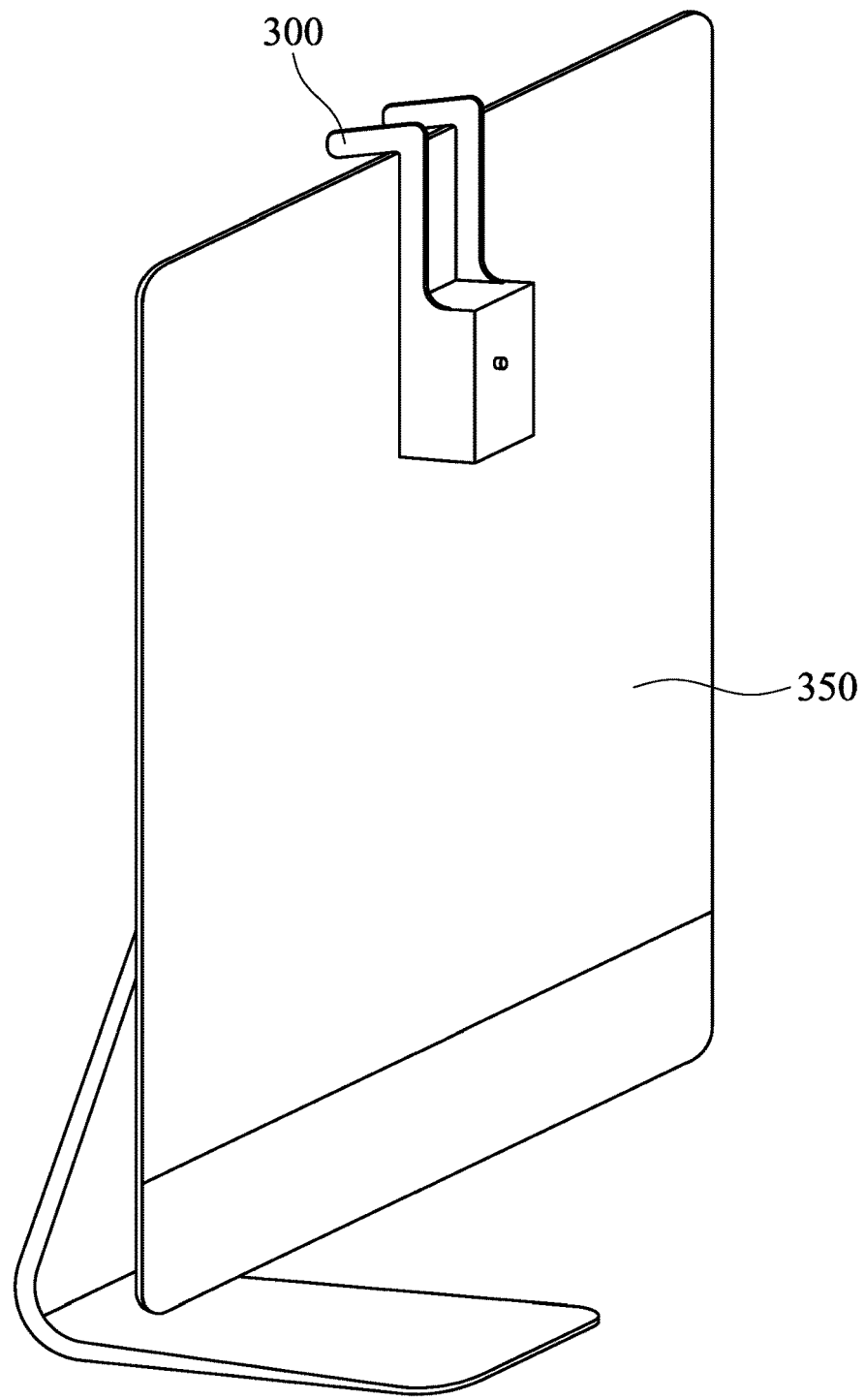

FIGS. 3A to 3C are schematic diagrams of the fault detection device in accordance with the second embodiment of the present invention. The fault detection device 200 has a housing 300, and the housing 300 is provided with an ear-hanging structure for fixing the fault detection device in front of the display screen in a suspension manner (as shown in FIG. 3C). As shown in FIG. 3A, the LED as the first warning device 231 is provided on a first surface 310 for displaying a first display signal (for example, a flashing or constant light LED) toward the operator. As shown in FIG. 3B, the sensors 211 to 213 are provided on a second surface 320 with respect to one of the first surfaces 310 to face the display screen to sense the change in the brightness value of the display screen. The display of the code or patterns may be presented in a horizontal or vertical manner while the display screen is testing, so that the sensors 211 to 213 will not be arranged horizontally or vertically which is shown in FIG. 3B in order to avoid an inaccurate determination. Herein, since the display screen is usually displayed in a left-to-right and top-down manner, in a preferred embodiment, the fault detection device 200 can be provided at the upper left of the display screen.

It should be noted that the fault detection device 200 may also be attached to the display screen in other ways, for example, through a suction cup or a clip.

FIG. 4 is a flowchart of a fault detection method in accordance with the first embodiment of the present invention. In step S401, the sensor 111 obtains the current brightness value of its location every first predetermined period of time. In step S402, the microprocessor 120 receives the sensing signal $S_S$ corresponding to the current brightness value from the sensor 111. In step S403, the microprocessor 120 determines whether the current brightness value is the same as the previous brightness value. If the current brightness value is different from the previous brightness value, the method returns to step S402, where the microprocessor 120 receives the sensing signal $S_S$ from the sensor 111 every first predetermined period of time. On the other hand, if the current brightness value is equal to the previous brightness value, the method proceeds to step S404, the microprocessor 120 enables the first warning unit 131 to generate the first warning signal. In step S405, the microprocessor 120 continuously determines whether the current brightness value is the same as the previous brightness value. If the current brightness value is different from the previous brightness value, the method proceeds to step S406, the microprocessor 120 disables the first warning unit and returns to step S402. On the other hand, if the current brightness value is equal to the previous brightness value for more than the second predetermined period of time, the method proceeds to step S407 where the microprocessor 120 enables the second warning unit 132 to generate the second warning signal.

FIG. 5 is a flowchart of a fault detection method in accordance with the second embodiment of the present invention. In step S501, the sensors 211 to 213 obtain the current brightness value of respective locations every first predetermined period of time. In step S502, the microprocessor 220 receives the sensing signals $S_{S1}$ to $S_{S3}$ corresponding to the first, second and third current brightness values from the sensors 211 to 213. In step S503, the microprocessor 220 determines whether the first, second and third current brightness values are the same as the first, second and third previous brightness values, respectively. If any one of the first, second and third current brightness values are different from the first, second and third previous brightness values, the method returns to step S502, the microprocessor 220 receives the sensing signals $S_{S1}$ to $S_{S3}$ from the sensors 211 to 213 every first predetermined period of time. On the other hand, if the first, second and third current brightness values are the same as the first, second and third previous brightness values, the method proceeds to step S504, the microprocessor 120 enables the first warning unit 231 to generate a first warning signal. In step S505, the microprocessor 220 continuously determines whether the first, second and third current brightness values are the same as the first, second, and third previous brightness values. If any one of the first, second and third current brightness values is different from the first, second and third previous brightness values, the method proceeds to step S506, the microprocessor 220 disables the first warning unit 231 and returns to step S502. On the other hand, if the first, second and third current brightness values are the same as the first, second and third previous brightness values for more than the second predetermined period of time, the method proceeds to step S507, the microprocessor 220 enables the warning unit 232 to generate the second warning signal.

As described above, the present invention provides fault detection devices and fault detection methods, when the electronic devices enters production stage, since the display content of the display screen will be changed with the test content, and the brightness of the display screen will also be changed. So that in the present invention, the brightness sensor is set in front of the display screen to monitor whether the brightness of the display screen is changed for determining whether the display screen is functioning properly. Moreover, by using two-stage detection, inaccurate detection and wasted time can be reduced, and the human resources can also be avoided being wasted to improve the efficiency of production. In addition, since the fault detection device can also be powered by a USB port of the measured electronic device, thus it is also possible to determine whether the measured electronic device is malfunctioning.

It will be apparent to those skilled in the art that various modifications and variations can be made to the structure disclosed without departing from the scope or spirit of the invention. In view of the foregoing, it is intended that the present invention covers modifications and variations of this invention, provided they fall within the scope of the following claims and their equivalents.

What is claimed is:
1. A fault detection device, adapted to an electronic device having a display screen, comprising:
 a first warning unit, generating a first warning signal;
 a second warning unit, generating a second warning signal;
 a first sensor, disposed in front of the display screen for obtaining and outputting a first current brightness value of the display screen every first predetermined period of time; and
 a microprocessor, coupled to the first warning unit, the second warning unit and the first sensor for comparing the first current brightness value with a first previous brightness value;
 wherein the microprocessor enables the first warning unit to generate the first warning signal when the first current brightness value is equal to the first previous brightness value, and the microprocessor enables the second warning unit to generate the second warning signal when the first current brightness value is equal to the first previous brightness value for more than a second predetermined period of time, wherein the second predetermined period of time is greater than the first predetermined period of time;
 wherein the first sensor is a light sensor; and
 wherein the first warning unit is an LED and the second warning unit is a buzzer.

2. The fault detection device as claimed in claim 1, wherein when the microprocessor determines that the first current brightness value is not equal to the first previous brightness value after enabling the first warning unit, the microprocessor disables the first warning unit.

3. The fault detection device as claimed in claim 1, further comprising:
 a second sensor, obtaining a second current brightness value of the display screen every first predetermined period of time; and
 a third sensor, obtaining a third current brightness value of the display screen every first predetermined period of time;
 wherein the microprocessor enables the first warning unit to generate the first warning signal when the microprocessor determines that the first current brightness value, the second current brightness value and the third current brightness value are respectively equal to the first previous brightness value, a second previous brightness value and a third previous brightness value, and the microprocessor enables the second warning unit to generate the second warning signal when the first current brightness value, the second current brightness value and the third current brightness value are respectively equal to the first previous brightness value, the second previous brightness value, and the third previous brightness value for more than the second predetermined period of time; and
 wherein the second sensor is the light sensor.

4. The fault detection device as claimed in claim 3, wherein the first sensor, the second sensor and the third sensor will not be arranged horizontally or vertically at the same time.

5. The fault detection device as claimed in claim 1, further comprising:
 a housing, having an ear-hanging structure, accommodating the first warning unit, the second warning unit, the first sensor and the microprocessor, and being mounted on the electronic device by the ear-hanging structure;
 wherein the first sensor is disposed on a first surface of the housing facing the display screen, and the first warning unit and the second warning unit are disposed on a second surface with respect to the first surface.

6. A fault detection method, adapted to an electronic device having a display screen, comprising:

obtaining, using a first sensor, a first current brightness value of the display screens every first predetermined period of time, wherein the first sensor is disposed in front of the display screen;

receiving, using a microprocessor, the first current brightness value from the first sensor; and comparing, using the microprocessor, the first current brightness value with a first previous brightness value;

when the first current brightness value is equal to the first previous brightness value, the microprocessor enables a first warning unit to generate a first warning signal by the microprocessor; and when the first current brightness value is equal to the first previous brightness value for more than a second predetermined period of time, enabling a second warning unit to generate a second warning signal by the microprocessor;

wherein the second predetermined period of time is greater than the first predetermined period of time;

wherein the first sensor is a light sensor; and wherein the first warning unit is an LED and the second warning unit is a buzzer.

7. The fault detection method as claimed in claim 6, wherein when the microprocessor determines that the first current brightness value is not equal to the first previous brightness value after enabling the first warning unit, the microprocessor enables the first warning unit.

8. The fault detection method as described in claim 6, further comprising:

obtaining, using a second sensor, a second current brightness value of the display screen every first predetermined period of time;

obtaining, using a third sensor, a third current brightness value of the display screen every first predetermined period of time;

when the microprocessor determines that the first current brightness value, the second current brightness value and the third current brightness value are respectively equal to the first previous brightness value, a second previous brightness value and a third previous brightness value, the microprocessor enables the first warning unit to generate the first warning signal; and when the microprocessor determines that the first current brightness value, the second current brightness value and the third current brightness value are respectively and continuously equal to the first previous brightness value, the second previous brightness value and the third previous brightness value for more than a second predetermined period of time, the microprocessor enables the second warning unit to generate the second warning signal; and wherein the second sensor is the light sensor.

9. The fault detection method as claimed claim 8, wherein the first sensor, the second sensor and the third sensor are not arranged horizontally or vertically at the same time.

10. A fault detection method as claimed in claim 6, wherein the first warning unit, the second warning unit, the first sensor and the microprocessor are accommodated in a housing, wherein the housing has an ear-hanging structure, and is mounted on the electronic device by the ear-hanging structure, the first sensor is disposed on a first surface of the housing facing the display screen, and the first warning unit and the second warning unit are disposed on a second surface with respect to the first surface.

* * * * *